United States Patent
Hashiba et al.

(10) Patent No.: US 8,974,379 B2
(45) Date of Patent: Mar. 10, 2015

(54) MEDICAL SYSTEMS FOR ACCESSING AN INTERNAL BODILY OPENING

(75) Inventors: Kiyoshi Hashiba, Sao Paulo (BR); Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1159 days.

(21) Appl. No.: 12/398,687

(22) Filed: Mar. 5, 2009

(65) Prior Publication Data

US 2009/0227836 A1 Sep. 10, 2009

Related U.S. Application Data

(60) Provisional application No. 61/034,376, filed on Mar. 6, 2008.

(51) Int. Cl.
*A61B 1/00* (2006.01)
*A61B 17/34* (2006.01)
*A61B 17/00* (2006.01)

(52) U.S. Cl.
CPC ..... *A61B 17/3421* (2013.01); *A61B 2017/3488* (2013.01); *A61B 2017/3419* (2013.01); *A61B 2017/00278* (2013.01)
USPC ........................................ 600/184

(58) Field of Classification Search
CPC .................. A61B 17/3421; A61B 2017/3445; A61B 17/3417; A61B 1/00137; A61B 2017/00278; A61B 2017/3488; A61B 2017/3419
USPC ................ 606/184, 185, 190, 191; 604/164.01–164.09, 164.1, 167.01; 600/104, 106, 201–204, 114, 184
See application file for complete search history.

(56) References Cited

U.S. PATENT DOCUMENTS

| | | | |
|---|---|---|---|
| 3,774,608 | A | 11/1973 | Wohler, Jr. |
| 3,915,171 | A | 10/1975 | Shermeta |
| 4,023,559 | A | 5/1977 | Gaskell |
| 4,224,929 | A | 9/1980 | Furihata |

(Continued)

FOREIGN PATENT DOCUMENTS

| | | |
|---|---|---|
| EP | 1062966 B1 | 1/2004 |
| EP | 1985226 A2 | 10/2008 |

(Continued)

OTHER PUBLICATIONS

International Search Report/Written Opinion for PCT/US2009/036173 mailed May 29, 2009.

(Continued)

*Primary Examiner* — Katrina Stransky
(74) *Attorney, Agent, or Firm* — Brinks Gilson & Lione

(57) ABSTRACT

Medical systems, devices and methods are provided for accessing a bodily opening that, among other things, are safe and reliable, and facilitate manipulation of a medical instrument. The medical access device generally includes an elongated flexible sheath and a port connected to the distal end of the flexible sheath. The sheath defines a sheath lumen and a longitudinal axis. The port has an interior surface defining a passageway and an exterior surface that is tapered in a distal direction. The passageway is in communication with the sheath lumen. The exterior surface of the port defines a radially opening channel sized to receive at least a portion of the tissue therein.

22 Claims, 3 Drawing Sheets

(56) References Cited

U.S. PATENT DOCUMENTS

| | | | |
|---|---|---|---|
| 4,249,535 A | 2/1981 | Hargest, III | |
| 4,315,509 A | 2/1982 | Smit | |
| 4,327,736 A | 5/1982 | Inoue | |
| 4,538,606 A | 9/1985 | Whited | |
| 4,664,114 A | 5/1987 | Ghodsian | |
| 4,676,778 A | 6/1987 | Nelson, Jr. | |
| 4,686,965 A | 8/1987 | Bonnet et al. | |
| 4,765,314 A | 8/1988 | Kolditz et al. | |
| 4,773,394 A | 9/1988 | Reichstein et al. | |
| 5,002,532 A | 3/1991 | Gaiser et al. | |
| 5,025,778 A | 6/1991 | Silverstein et al. | |
| 5,158,543 A | 10/1992 | Lazarus | |
| 5,197,971 A | 3/1993 | Bonutti | |
| 5,217,001 A | 6/1993 | Nakao et al. | |
| 5,279,565 A | 1/1994 | Klein et al. | |
| 5,354,302 A | 10/1994 | Ko | |
| 5,380,304 A | 1/1995 | Parker | |
| 5,389,074 A | 2/1995 | Parker et al. | |
| 5,400,770 A | 3/1995 | Nakao et al. | |
| 5,540,658 A * | 7/1996 | Evans et al. | 604/101.04 |
| 5,707,355 A | 1/1998 | Zimmon | |
| 5,814,073 A | 9/1998 | Bonutti | |
| 5,824,071 A * | 10/1998 | Nelson et al. | 606/194 |
| 5,836,913 A * | 11/1998 | Orth et al. | 604/107 |
| 5,846,182 A | 12/1998 | Wolcott | |
| 5,876,325 A | 3/1999 | Mizuno et al. | |
| 5,882,345 A | 3/1999 | Yoon | |
| 5,906,579 A | 5/1999 | Vander Salm et al. | |
| 6,030,365 A | 2/2000 | Laufer | |
| 6,156,006 A | 12/2000 | Brosens et al. | |
| 6,234,958 B1 | 5/2001 | Snoke et al. | |
| 6,315,733 B1 | 11/2001 | Zimmon | |
| 6,488,692 B1 | 12/2002 | Spence et al. | |
| 6,535,764 B2 | 3/2003 | Imran et al. | |
| 6,551,270 B1 | 4/2003 | Bimbo et al. | |
| 6,572,629 B2 | 6/2003 | Kalloo et al. | |
| 6,652,492 B1 | 11/2003 | Bell et al. | |
| 6,689,062 B1 | 2/2004 | Mesallum | |
| 6,918,871 B2 | 7/2005 | Schulze | |
| 6,988,987 B2 * | 1/2006 | Ishikawa et al. | 600/114 |
| 7,128,708 B2 | 10/2006 | Saadat et al. | |
| 7,204,841 B2 * | 4/2007 | Green | 606/139 |
| 7,273,451 B2 | 9/2007 | Sekine et al. | |
| 7,377,897 B1 * | 5/2008 | Kunkel et al. | 600/184 |
| 7,575,548 B2 | 8/2009 | Takemoto et al. | |
| 7,615,003 B2 | 11/2009 | Stefanchik et al. | |
| 7,615,005 B2 | 11/2009 | Stefanchik et al. | |
| 7,637,905 B2 | 12/2009 | Saadat et al. | |
| 7,637,919 B2 | 12/2009 | Ishikawa et al. | |
| 7,654,951 B2 | 2/2010 | Ishikawa | |
| 7,717,847 B2 | 5/2010 | Smith | |
| 7,721,742 B2 | 5/2010 | Kalloo et al. | |
| 7,735,489 B2 | 6/2010 | Mikkaichi et al. | |
| 7,785,251 B2 | 8/2010 | Wilk | |
| 7,785,333 B2 | 8/2010 | Miyamoto et al. | |
| 2001/0049503 A1 | 12/2001 | Estabrook et al. | |
| 2002/0022764 A1 | 2/2002 | Smith et al. | |
| 2002/0022851 A1 | 2/2002 | Kalloo et al. | |
| 2002/0193806 A1 | 12/2002 | Moenning et al. | |
| 2003/0065359 A1 | 4/2003 | Weller et al. | |
| 2003/0093104 A1 | 5/2003 | Bonner et al. | |
| 2003/0181938 A1 * | 9/2003 | Roth et al. | 606/191 |
| 2003/0216613 A1 | 11/2003 | Suzuki et al. | |
| 2003/0225312 A1 | 12/2003 | Suzuki et al. | |
| 2003/0229296 A1 | 12/2003 | Ishikawa | |
| 2003/0233109 A1 * | 12/2003 | Green | 606/144 |
| 2004/0193114 A1 * | 9/2004 | Elbert et al. | 604/164.1 |
| 2004/0249367 A1 | 12/2004 | Saadat et al. | |
| 2005/0056292 A1 | 3/2005 | Cooper | |
| 2005/0101837 A1 | 5/2005 | Kalloo et al. | |
| 2005/0107664 A1 | 5/2005 | Kalloo et al. | |
| 2005/0149078 A1 | 7/2005 | Vargas et al. | |
| 2005/0251176 A1 | 11/2005 | Swanstrom et al. | |
| 2005/0277945 A1 | 12/2005 | Saadat et al. | |
| 2006/0015006 A1 | 1/2006 | Laurence et al. | |
| 2006/0100480 A1 | 5/2006 | Ewers et al. | |
| 2006/0135971 A1 | 6/2006 | Swanstrom et al. | |
| 2006/0135984 A1 | 6/2006 | Kramer et al. | |
| 2006/0135985 A1 | 6/2006 | Cox et al. | |
| 2006/0178560 A1 | 8/2006 | Saadat et al. | |
| 2006/0200004 A1 | 9/2006 | Wilk | |
| 2006/0211919 A1 | 9/2006 | Wilk | |
| 2006/0212063 A1 | 9/2006 | Wilk | |
| 2006/0229653 A1 | 10/2006 | Wilk | |
| 2006/0237022 A1 | 10/2006 | Chen et al. | |
| 2006/0237023 A1 | 10/2006 | Cox et al. | |
| 2006/0241344 A1 | 10/2006 | Wilk | |
| 2006/0241480 A1 | 10/2006 | Wilk | |
| 2006/0241570 A1 | 10/2006 | Wilk | |
| 2006/0241651 A1 | 10/2006 | Wilk | |
| 2006/0247672 A1 * | 11/2006 | Vidlund et al. | 606/190 |
| 2006/0252997 A1 | 11/2006 | Wilk | |
| 2006/0253123 A1 | 11/2006 | Wilk | |
| 2006/0258909 A1 | 11/2006 | Saadat et al. | |
| 2007/0038224 A1 | 2/2007 | Ortiz | |
| 2007/0051380 A1 | 3/2007 | Pasricha | |
| 2007/0106313 A1 | 5/2007 | Golden et al. | |
| 2007/0163596 A1 | 7/2007 | Mikkaichi et al. | |
| 2007/0167675 A1 | 7/2007 | Miyamoto et al. | |
| 2007/0167676 A1 | 7/2007 | Miyamoto et al. | |
| 2007/0167967 A1 | 7/2007 | Mikkaichi et al. | |
| 2007/0203517 A1 * | 8/2007 | Williams et al. | 606/191 |
| 2007/0260117 A1 | 11/2007 | Zwolinski et al. | |
| 2008/0021277 A1 | 1/2008 | Stefanchik | |
| 2008/0039786 A1 | 2/2008 | Epstein et al. | |
| 2008/0051735 A1 | 2/2008 | Measamer et al. | |
| 2008/0058650 A1 | 3/2008 | Saadat et al. | |
| 2008/0097157 A1 | 4/2008 | Ortiz et al. | |
| 2008/0119868 A1 | 5/2008 | Sharp et al. | |
| 2008/0161644 A1 | 7/2008 | Ghabrial | |
| 2008/0183039 A1 | 7/2008 | Long et al. | |
| 2008/0228029 A1 | 9/2008 | Mikkaichi et al. | |
| 2008/0249358 A1 | 10/2008 | Motai et al. | |
| 2008/0249416 A1 | 10/2008 | Sato | |
| 2008/0249474 A1 | 10/2008 | Baker | |
| 2008/0255422 A1 | 10/2008 | Kondoh et al. | |
| 2008/0255423 A1 | 10/2008 | Kondo et al. | |
| 2008/0262294 A1 | 10/2008 | Ewers et al. | |
| 2008/0262300 A1 | 10/2008 | Ewers | |
| 2008/0262302 A1 | 10/2008 | Azarbarzin et al. | |
| 2008/0287743 A1 | 11/2008 | Smith et al. | |
| 2008/0287963 A1 | 11/2008 | Rogers et al. | |
| 2008/0287983 A1 | 11/2008 | Smith et al. | |
| 2008/0300547 A1 | 12/2008 | Bakos | |
| 2008/0319258 A1 | 12/2008 | Thompson | |
| 2009/0054728 A1 | 2/2009 | Trusty | |
| 2009/0112062 A1 * | 4/2009 | Bakos | 600/114 |
| 2009/0143643 A1 | 6/2009 | Weitzner et al. | |
| 2009/0149714 A1 | 6/2009 | Bonadio | |
| 2009/0192465 A1 | 7/2009 | Smith | |
| 2009/0259141 A1 | 10/2009 | Ewers et al. | |
| 2009/0259172 A1 | 10/2009 | Yamaoka et al. | |
| 2009/0275798 A1 | 11/2009 | Naito | |
| 2009/0275967 A1 | 11/2009 | Stokes et al. | |
| 2009/0276055 A1 | 11/2009 | Harris et al. | |
| 2010/0010298 A1 | 1/2010 | Bakos et al. | |
| 2010/0010299 A1 | 1/2010 | Bakos et al. | |
| 2010/0010303 A1 | 1/2010 | Bakos | |
| 2010/0036200 A1 | 2/2010 | Okada | |
| 2010/0042078 A1 | 2/2010 | Okada | |
| 2010/0069716 A1 | 3/2010 | Chin et al. | |
| 2010/0081863 A1 | 4/2010 | Hess et al. | |
| 2010/0081864 A1 | 4/2010 | Hess et al. | |
| 2010/0081871 A1 | 4/2010 | Widenhouse et al. | |
| 2010/0081877 A1 | 4/2010 | Vakharia | |
| 2010/0081880 A1 | 4/2010 | Widenhouse et al. | |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |
| 2010/0114033 A1 | 5/2010 | Fischvogt | |
| 2010/0130817 A1 | 5/2010 | Conlon | |
| 2010/0130821 A1 | 5/2010 | Rosemurgy et al. | |
| 2010/0160729 A1 | 6/2010 | Smith et al. | |

(56) References Cited

U.S. PATENT DOCUMENTS

2010/0160735 A1 6/2010 Bakos
2010/0168519 A1 7/2010 Matsuo
2010/0168522 A1 7/2010 Wenchell et al.

FOREIGN PATENT DOCUMENTS

| GB | 2145932 | 4/1985 |
| JP | 2000051361 | 2/2000 |
| JP | 2001009037 | 1/2001 |
| WO | WO 98/50104 A | 11/1998 |
| WO | WO 2004/000410 A | 12/2003 |
| WO | WO 2004/037097 A | 5/2004 |
| WO | WO 2005/023358 A1 | 3/2005 |
| WO | WO 2006/029370 A2 | 3/2006 |
| WO | WO 2007/019117 A | 2/2007 |
| WO | WO 2007/038715 A | 4/2007 |
| WO | WO 2009/140594 A2 | 11/2009 |

OTHER PUBLICATIONS

Article 34 Amendments in PCT/US2009/036173.
Supplemental Letter and Amendments Under Article 34 for PCT/US2009/036173.
International Preliminary Report on Patentability for PCT/US2009/026173 mailed May 7, 2010.
International Search Report/Written Opinion for PCT/US2010/022572 mailed May 21, 2010.
E. Dubcenco, et al., The development of a novel intracolonic occlusion balloon for transcolonic natural orifice transluminal endoscopic surgery: description of the technique and early experience in a porcine model (with Videos); Gastrointestinal Endoscopy, vol. 68, No. 4, 2008, pp. 760-766.
International Search Report/Written Opinion for PCT/US2008/079199 mailed Jan. 22, 2009.
Article 34 Amendments in PCT/US2008/079199.
International Preliminary Report on Patentability for PCT/US2008/079199 mailed Jan. 15, 2010.

\* cited by examiner

MEDICAL SYSTEMS FOR ACCESSING AN INTERNAL BODILY OPENING

CROSS-REFERENCE TO RELATED APPLICATIONS

This application claims the benefit of U.S. Provisional Application Ser. No. 61/034,376 filed on Mar. 6, 2008, entitled "SYSTEMS, DEVICES AND METHODS FOR ACCESSING A BODILY OPENING" the entire contents of which are incorporated herein by reference.

FIELD OF THE INVENTION

The present invention relates generally to medical systems, devices and methods to access a bodily opening via a bodily lumen, such as an opening in a wall of the gastrointestinal tract accessed via the tract, for deployment of an endoscope and/or other medical devices.

BACKGROUND OF THE INVENTION

Openings in bodily walls may be formed to gain access to adjacent structures of the body, such techniques being commonly referred to as translumenal procedures. For example, culdoscopy was developed over 70 years ago, and involves transvaginally accessing the peritoneal cavity by forming an opening in the cul de sac. This access to the peritoneal cavity allows medical professionals to visually inspect numerous anatomical structures, as well as perform various procedures such as biopsies, tubal ligations, or other operations, all in a minimally invasive manner. Many translumenal procedures for gaining access to various body cavities using other bodily lumens have also been developed. For example, the bodily lumens of the gastrointestinal tract are often endoscopically explored and can be utilized to provide access to the peritoneal cavity and other body cavities. U.S. patent application Ser. No. 11/946,565 filed Feb. 28, 2007, discloses such a procedure, and is incorporated herein by reference in its entirety.

Although translumenal procedures are minimally invasive, there are also various risks involved. For example, when an opening is formed in a bodily wall of the gastrointestinal tract, such as in the stomach or intestines, spillage of the stomach contents, intestinal contents or other bodily fluids into the adjacent body cavity can occur. Travel of bacteria laden fluids outside of the gastrointestinal tract may cause unwanted and sometimes deadly infection. Traditional overtubes have been used to protect the mouth and esophagus while delivering an endoscope to the stomach. However, these overtubes do not seal to the gastric wall. Furthermore, traditional overtubes are quite rigid, can themselves harm the throat or esophagus, and restrict the ability to manipulate the endoscope as desired.

BRIEF SUMMARY OF THE INVENTION

The present invention provides medical systems, devices and methods for accessing a bodily opening that are, among other things, safe and reliable, and that aid in the manipulation of the endoscope or other medical tools. A medical access device for accessing a bodily opening is provided in accordance with the teachings of the present invention, and generally includes an elongated flexible sheath and a port connected to the distal end of the flexible sheath. The sheath defines a sheath lumen and a longitudinal axis. The port has an interior surface defining a passageway and an exterior surface that is tapered in a distal direction. The passageway is in communication with the sheath lumen. The exterior surface of the port defines an annular channel that opens radially and is sized to receive at least a portion of the tissue therein.

According to more detailed aspect of the medical access device, channel is annular and extends around the port. The port has a proximal portion and a distal portion, and the channel is preferably formed in the proximal portion of the port. The channel preferably has a width that is less than or equal to a thickness of the tissue. The port may be formed of an elastomer, and is deflectable. The taper on the exterior surface of the port may be curved or conical.

A medical system is also provided in accordance with the teachings of the present invention. The medical system includes a medical device such as those described above, as well as a pusher. The pusher defines a pusher lumen that is sized to receive the elongated flexible sheath therein. The port defines a pushing surface sized and positioned to abut the pusher. According to more detailed aspects, the port projects radially from the flexible sheath to define the pushing surface. The pushing surface is preferably formed on a proximal portion of the port and is proximally facing. The medical system may further include a medical instrument sized to be translated through the sheath lumen and the passageway.

A method for accessing a bodily opening defined by tissue, via a bodily lumen, is also provided in accordance with the teachings of the present invention. A medical system is provided, the system including a medical access device, a pusher, and a medical instrument such as those described above. The medical access device is translated through the bodily lumen. The pusher is translated through the bodily lumen such that the flexible sheath of the medical access device is received within the pusher lumen. The medical access device is engaged with the pusher to distally move the medical access device through the bodily opening such that the tissue is received within the channel of the port. The medical instrument is translated through the sheath lumen to a distal side of the bodily opening.

According to more detailed aspects of the method, the flexible sheath of the medical access device is positioned within the pusher lumen, and the medical access device and pusher are translated together through the bodily lumen. When the medical instrument is positioned within the sheath lumen, the medical instrument, medical access device, and pusher may be translated together through the bodily lumen. The medical instrument is preferably used to form the opening in the tissue. The medical instrument may also include an endoscope, and further comprises the steps of translating a surgical tool through the distal end of the overtube and forming the bodily opening with the surgical tool. The medical instrument may further include a dilation device that is translated through the distal end of the sheath and enlarges the bodily opening. The medical access device may be retracted by forcefully translating the medical access device proximally.

DETAILED DESCRIPTION OF THE INVENTION

Figure 1:
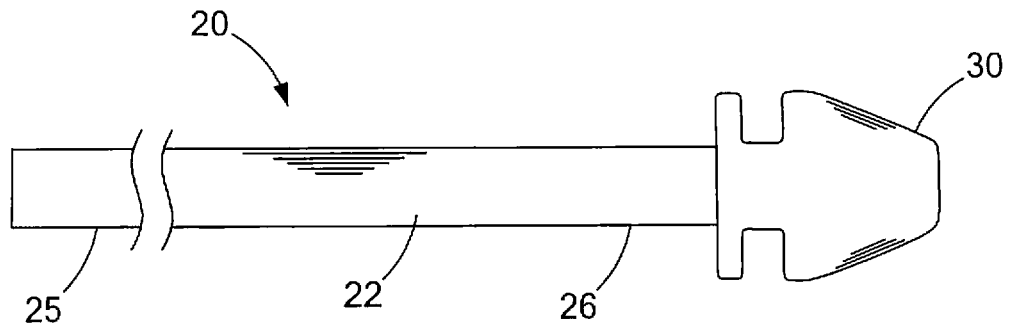
FIG. 1 is a side view of a medical access device constructed in accordance with the teachings of the present invention.
Figure 2:
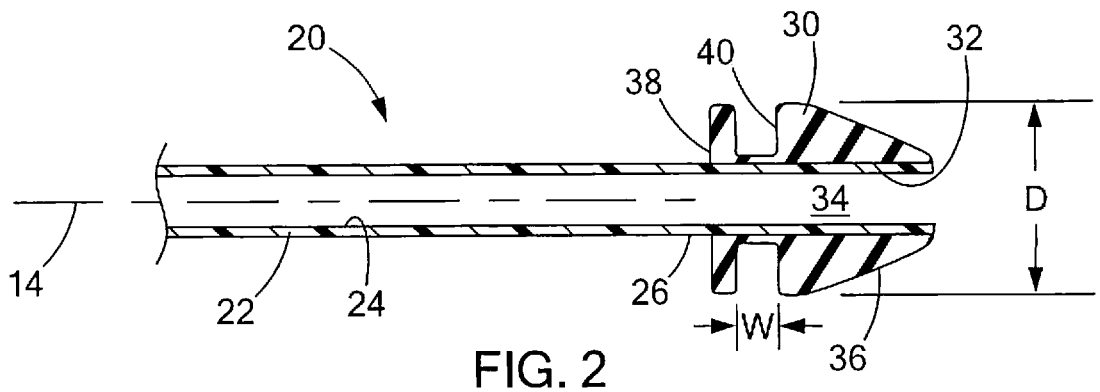
FIG. 2 is a cross-sectional view of the medical access device depicted in FIG. 1.
Figure 3:
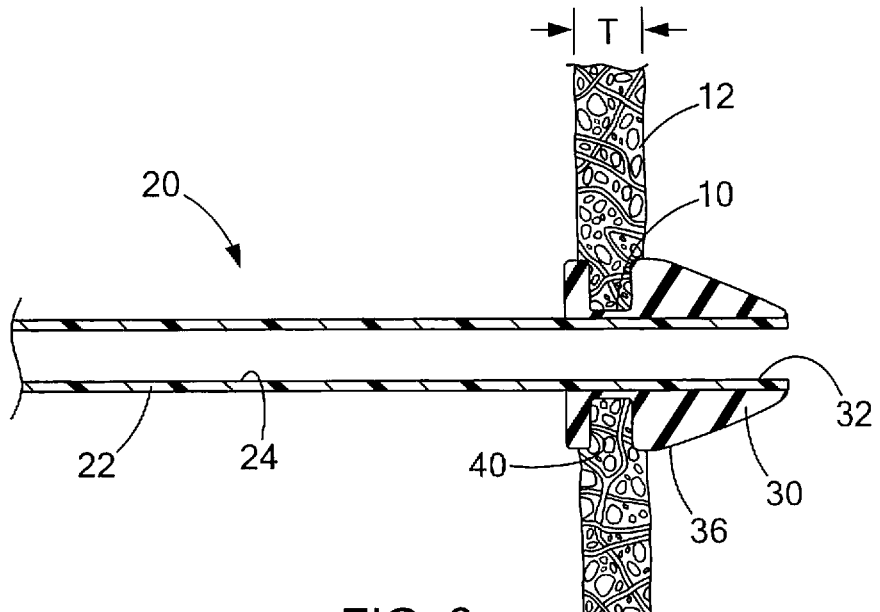
FIG. 3 is a cross-sectional view showing the medical access device of FIGS. 1 and 2 positioned within a bodily opening.

Turning now to the figures, FIGS. 1-3 depict various views of a medical access device 20 for accessing a bodily opening 10 formed in tissue 12 (FIG. 3). The medical access device 20 generally includes an elongated flexible sheath 22 and a port 30. The elongated flexible sheath 22 generally defines a sheath lumen 24 and a longitudinal axis 14. The diameter of the sheath lumen 24 is sized to receiving a medical instrument such as an endoscope or catheter based device, and preferably is in the range of about 2 mm to about 20 mm. The flexible sheath 22 includes a proximal end 25 and a distal end 26 and has a length suitable for endoscopic exploration. The port 30 is connected to the distal end 26 of the flexible sheath 22. The port 30 has an interior surface 32 defining a passageway 34. The port also defines an exterior surface 36 that tapers in the distal direction.

As shown in the figures, the exterior surface 36 of the port 30 is generally conical, and in particular a distal portion of the port 30 is frusto-conical, however it will be recognized by those skilled in the art that the exterior surface 36 could take a curved shape such as a convex or concave curvature, a complex curvature, or even be cylindrical, while keeping within the scope and spirit of the present invention. The passageway 34 of the port 30 is in communication with the sheath lumen 24. As shown, the interior surface 32 defining the passageway 34 is sized to completely receive the flexible sheath 22, although it will be recognized that the flexible sheath may end at any point along the length of the port 30 and its passageway, or even be directly connected to a proximal end surface 38 of the port 30. The flexible sheath 22 and port 30 may be connected by various known methods, including adhesives, molding techniques such as overmolding, sewing the two components together, utilizing other mechanical fasteners, or using welding techniques such as vibration welding.

Figure 8:
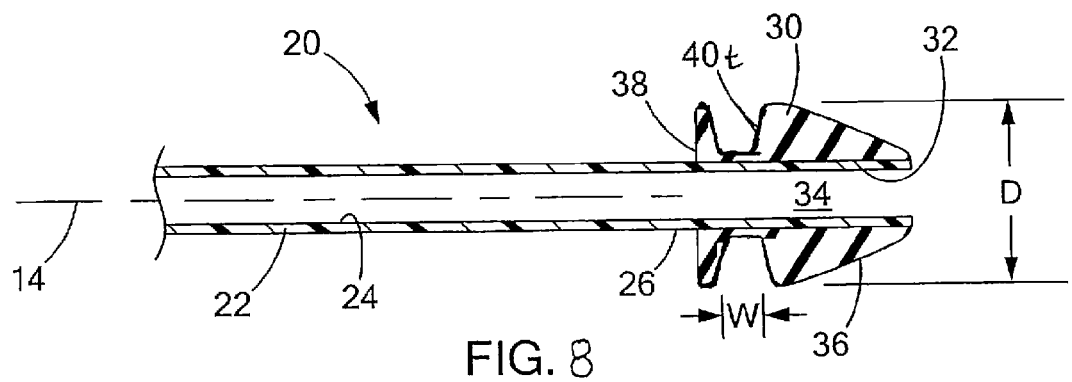
FIG. 8 is a cross-sectional view of an alternate embodiment of the medical access device depicted in FIG. 1.

As best seen in FIGS. 2 and 3, the port 30 further defines a channel 40 for connecting the medical access device 20 to the tissue 12 at its opening 10. More particularly, a proximal portion of the port (i.e. proximal to the sloped exterior surface 36 of the port 30) defines the channel 40 which has an annular shape extending around the port 30. The channel 40 is radially opening as shown. The port 30 generally has an outer diameter D as shown in FIG. 2, which preferably is in the range of about 2 mm to about 30 mm, and most preferably about 5 mm to about 20 mm. The channel 40 has an average width W that is preferably about less than or about equal to a thickness T of the tissue 12, and typically in the range of about 1 mm to about 7 mm. The channel 40 may also taper in the radial direction, and as shown in the embodiment of FIG. 8, the channel 40 tapers at about 2° to about 20°, and narrows in the radially inward direction. The depth of the channel 40 (e.g. the outer diameter D minus the reduced diameter of the port 30 in the area of the channel 40) is preferably in the range of about 2 mm to about 20 mm.

As shown in FIG. 3, due to the natural elasticity of the tissue 12, the tissue will extend into the channel 40 and may be partially compressed therein due to the size of the channel 40. This provides for a secure and fluid tight interconnection between the medical access device 20 and the tissue 12 by way of the port 30. The port 30 is preferably formed of an elastomer such as rubber or Santoprene®. As such, the port 30 is deflectable while being sufficiently atraumatic and sealing to the tissue 12 defining the bodily opening 10. Likewise, even though the channel 40 may have rather large depth, the flexibility of the port 30, and especially the proximal portion adjacent the channel 40, allows the port 30 to deform and deflect during both attachment to the tissue 12 and removal therefrom. For example, the flexibility of the port 30 allows the interior surface 32 and passageway 34 to collapse, thereby reducing the outer diameter of the port 30.

The elongated flexible sheath 22 of the medical access device 20 is preferably formed of a flexible plastic such as fluoroplastics, polyethylenes (high, medium or low density), Teflon™, polyethylene ether ketones (PEEK), polyurethanes, silicones or polyamides such as Nylon™. The structure of the flexible sheath 22 can include multi-layer or single layer constructions with or without reinforcement wires, coils or filaments. Likewise, a polyvinylchloride (PVC) coating may also be employed for increased durability, without making the sheath 22 too rigid. By utilizing a flexible polymer, manipulation and operation of the endoscope 52 or other medical instrument is not compromised. Accordingly, not only can the medical system 50 facilitate operation of the medical instrument, but navigation deeper within the gastrointestinal tract via a natural bodily opening is possible. At the same time, the medical system 50 is easy to deploy and provides a secure engagement and fluidic seal with the internal bodily opening in the tissue that can prevent unwanted travel of bacteria laden fluids including the gastrointestinal tract.

Figure 4:
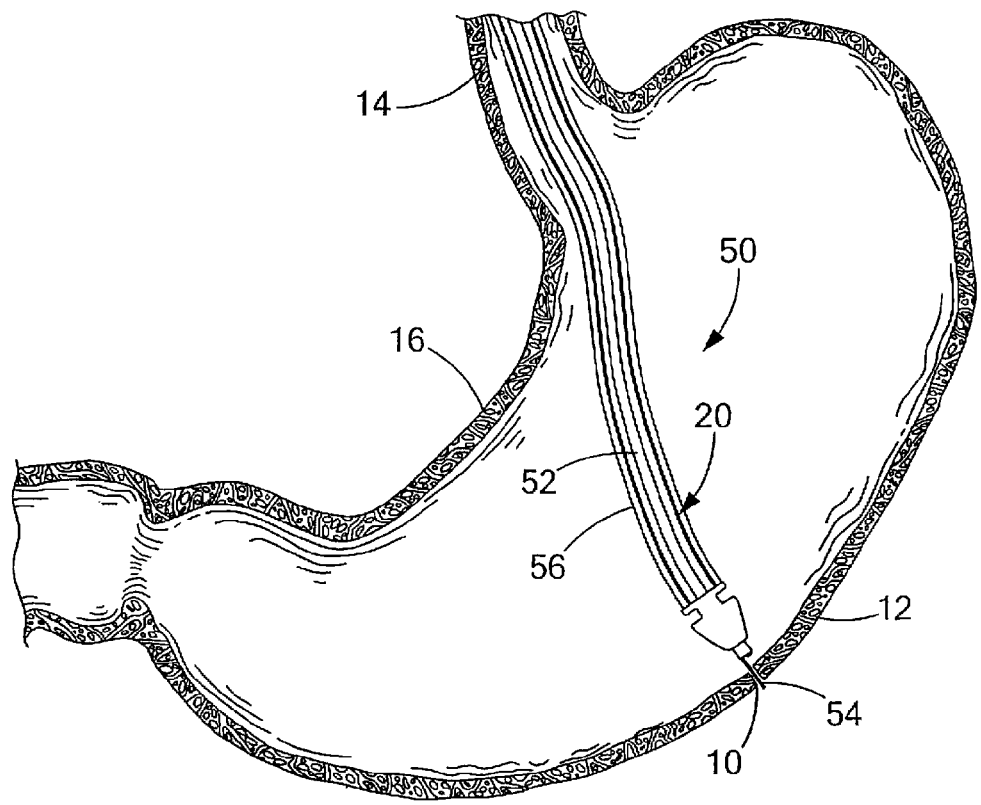
FIG. 4 is a schematic view, partially in cross-section and partially in elevation, showing a medical system including the medical access device of FIGS. 1-3.

Turning now to FIG. 4, a medical system 50 has been depicted which includes the medical access device 20 discussed above. In addition to the medical access device 20, a medical instrument such as an endoscope 52 is employed in conjunction therewith. Preferably, the medical system 50 also includes a surgical tool 54 which can be used through the working channel of the endoscope 52, in order to manually form the opening 10 in the tissue 12. In FIG. 4, introduction of the medical system 50 has been depicted as occurring through a bodily lumen such as the esophagus 14, for access to the stomach 16. As such, the opening formed by the surgical tool 54 is formed in the tissue 12 which represents the gastric wall.

The medical system 50 also preferably includes a pusher 56 which is generally stronger and more rigid than the flexible sheath 22 of the medical access device 20. The proximal end surface 38 of the port 30 generally defines a pushing surface for being pressed upon by the pusher 56, although it will be recognized that such a pushing surface may be formed on other portions or by other structures of the port which project radially from the flexible sheath 20 to define a pushing surface. The pusher 56 is structured to engage the pushing surface 38 of the port 30. The pusher 56 is therefore utilized to assist in placement of the medical access device 20, as will be described in further detail herein below.

While the medical system 20 has been depicted as including the endoscope 52 as the medical instrument, many different medical instruments may be used in conjunction with the medical access device 20, such as wire guides, catheters, needles, device deployment systems, biopsy devices and the like. For example, in FIG. 4 the opening 12 in the tissue 14 has been depicted as formed utilizing a surgical tool 54, which can be employed in conjunction with the medical access device 20, and with or without the endoscope 52.

The surgical tool 52 is preferably an electrosurgical cutting tool that has been traversed through a working channel of the endoscope 52, although it will be recognized by those skilled in the art that any type of cutting device may be employed to form the opening 12. The surgical tool 26 includes a cutting tip which projects from a distal end of the medical access device 20 for forming the opening 12. While the opening 12 has been described as an intentionally formed perforation, it will be recognized by those skilled in the art that the bodily opening 12 may be unintentionally formed or naturally occurring. Alternatively, bodily opening 12 may be a natural opening that is part of the gastrointestinal tract or other bodily lumen, such as the openings at the esophageal sphincter, the pylorus sphincter, the sphincter of oddii, the ileocecal valve, or the anus.

A method for accessing the bodily opening 10 via a bodily lumen will now be described with reference to FIGS. 4-7. By way of example, the bodily lumen has been described herein as the portion of the gastrointestinal tract including the mouth, esophagus 14 and stomach 16. First, the medical system 50 is provided, namely the medical access device 20, the pusher 56, and a medical instrument such as the endoscope 52. Generally, the pusher 56 is advanced over the proximal end of the medical access device 20 such that the flexible sheath 22 is positioned within the pusher lumen 58. The medical instrument 52 is positioned with the sheath lumen 24, and preferably such that it projects from the distal end of the medical access device 20 for using in visualizing the target site in the stomach 16. Medical access device 20, medical instrument 52 and pusher 56 are translated together through the bodily lumen 14 to a position proximate the tissue 12, as depicted in FIG. 4. The surgical cutting tool 54 is then deployed through the working channel of the endoscope 52 to form the opening 10 within the tissue 12. It will be recognized that at this point in the method, the pusher 56 may not be needed to advance the medical system 50, as the flexible medical access device 20 will be at least somewhat reinforced by the endoscope 52. As such, the medical access device 20 and/or the endoscope 52 may be advanced to the tissue 12 to form the opening 10, without using the pusher 56.

Figure 5:
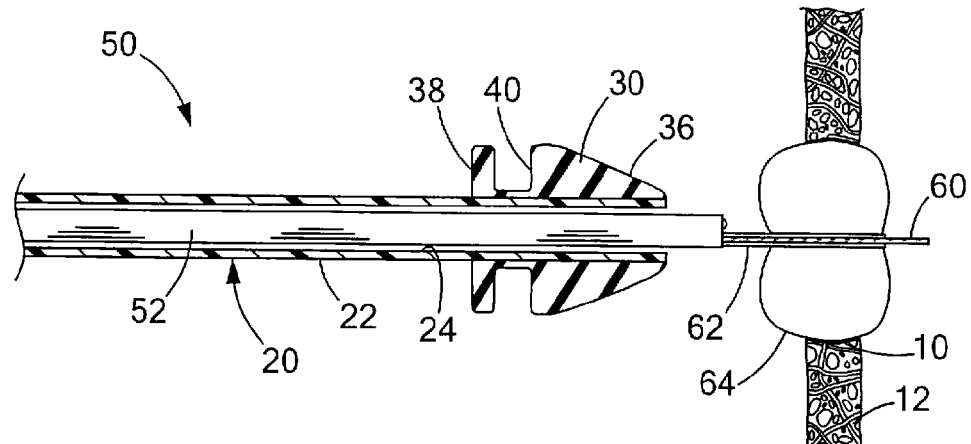
FIG. 5 is a cross-sectional view showing the medical system.
Figure 6:
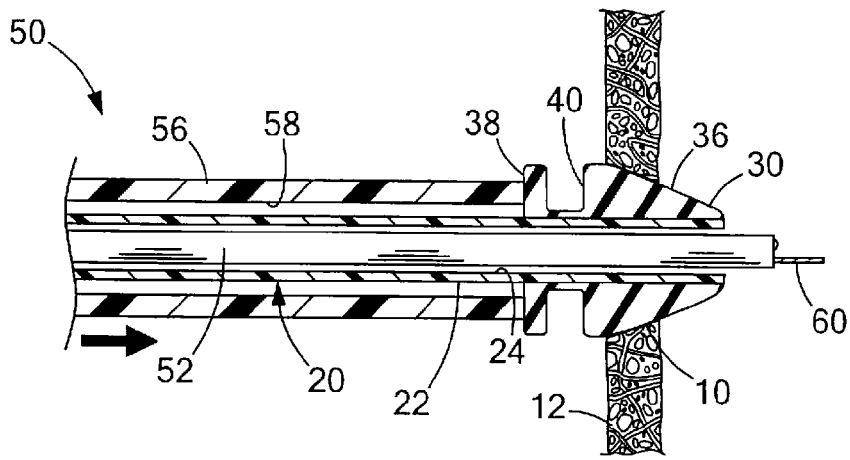
FIG. 6 is a cross-sectional view showing deployment of the medical system.
Figure 7:
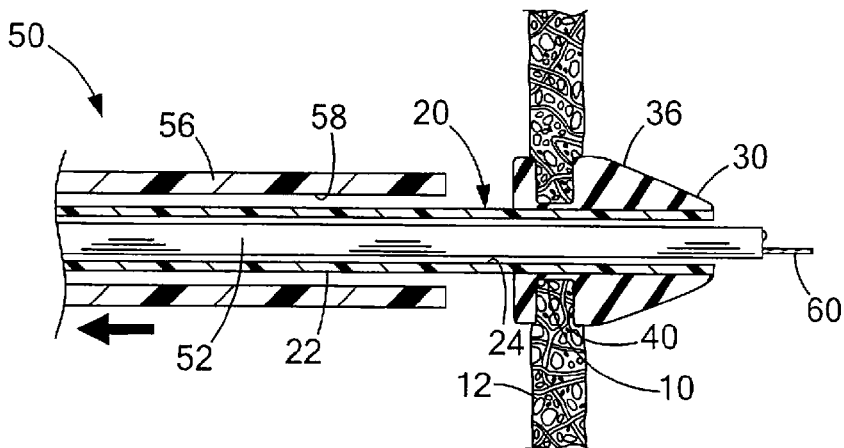
FIG. 7 is another cross-sectional view showing deployment of the medical system.

As best seen in FIG. 5, the surgical tool 54 is preferably withdrawn, and a wire guide 60 can be advanced through the opening 10. Similarly, a dilation device 62, such as a catheter having a dilation balloon 64, may then be translated through the working channel of the endoscope 52 over the wire guide 60. As is known in the art, the dilation device 62 may be utilized by inflating the balloon 64 or other dilation elements to expand or otherwise enlarge the opening 10 formed in the tissue 12. Depending upon the type of surgical cutting tool 54 that is employed, dilation of the opening 10 that may or may not be necessary. Preferably, the opening 10 is sized to be less than or about equal to the diameter D of the port 30.

The pusher 60 is translated to engage the proximal end surface 38 of the port 30 and advance the medical access device 20 through the opening 10 in the tissue. The tapered exterior surface 36 of the port 30 will serve to guide the medical access device 20, until the tissue 12 reaches the channel 40 formed in the proximal portion of the port 30. As previously noted, the natural elasticity of the tissue 12 will cause the tissue to enter the channel 40 and engage the port 30, thereby securely connecting the medical access device 20 to the tissue 12. The pusher 56 may then be withdrawn proximally and removed.

The flexible nature of the sheath 22 permits full manipulation of the endoscope 52 or other medical instrument. The wire guide 60 may be left in place to facilitate use of the endoscope 52 or may be removed. Many different medical instruments may be used in conjunction with the medical access device 20, such as wire guides, catheters, needles, device deployment systems, catheter-based interventional devices, biopsy devices, graspers and the like. The endoscope 52 provides a visualization system which can be used during all stages of the procedures described herein, including to select a site within the tissue for forming a perforation, guiding the medical system 50 through that opening, and then performing additional procedures or simply exploring on the distal side of the tissue 12. However, other visualization systems may be employed including catheter-based visual systems or other fiber optic devices. Finally, it should also be noted that the medical system 50 and placement of the medical access device 20 may also be used in conjunction with other monitoring techniques such as fluoroscopy, ultrasound or the like. As such, either the distal end of flexible tube 22 or the port 30 may have appropriate metals or other materials embedded therein or attached thereto that can be sensed by such monitoring systems.

Upon completion of the exploration and/or procedure on the distal side of opening 10, the medical instrument is withdrawn and the medical access device 20 is forcefully pulled proximally to cause the tissue 12 to exit the channel 40. An appropriate suturing tool may be utilized to close the opening 10 if needed. Exemplary suturing devices and perforation closure methods are disclosed in copending U.S. patent application Ser. No. 11/946,565 filed Nov. 28, 2007, Ser. No. 12/191,277 filed Aug. 13, 2008, Ser No. 12/191/001 filed Aug. 13, 2008 and Ser. No. 12/125,525 filed May 22, 2008, disclosures of which are hereby incorporated by reference in their entireties.

Accordingly, it will be seen that the medical systems, devices and methods of the present invention provide access to a bodily opening in a manner that is safe, reliable and easily repeatable. An endoscope or various other medical instruments may be repeatedly passed through the medical access device to access the cavities and structures on a distal side of the opening, as needed. Further, the medical access device is easily deployable, provides an effective fluidic seal with the tissue defining the opening, and is easily removed. All the while, manipulation and operation of an endoscope or other medical instrument is not hindered or compromised.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. The use of the terms seal or fluidic seal do not require that the barrier is completely leak-proof, but that it substantially prevents the flow of fluid or other contents therethrough. All such modifications and variations are within the scope of the invention as determined by the appended claims when interpreted in accordance with the breadth to which they are fairly, legally, and equitably entitled.

The invention claimed is:

1. A medical access device for accessing a bodily opening defined by tissue, the medical access device comprising:
   an elongated flexible sheath defining a sheath lumen and having a longitudinal axis, the flexible sheath having a proximal end and a distal end;
   a port non-detachably affixed to the distal end of the flexible sheath, the port having an interior surface defining a passageway and an exterior surface tapered in a distal direction, the passageway receiving the distal end of the sheath therein and being in communication with the sheath lumen, the port having an annular body defining the interior and exterior surfaces and substantially filling the space between the exterior surface of the port and the distal end of the flexible sheath, the exterior surface defining an annular channel opening radially and sized to receive at least a portion of the tissue therein.

2. The medical access device of claim 1, wherein the channel has a width that tapers in a radial direction.

3. The medical access device of claim 1, wherein the port has a proximal portion and a distal portion, and wherein the channel is formed in the proximal portion of the port.

4. The medical access device of claim 1, wherein the channel has a width that is less than or equal to a thickness of the tissue.

5. The medical access device of claim 1, wherein the port is formed of an elastomer.

6. The medical access device of claim 1, wherein the port is deflectable.

7. The medical access device of claim 1, wherein the exterior surface is conical.

8. The medical access device of claim 1, wherein the port is formed by a solid annular body extending around the passageway.

9. The medical access device of claim 1, wherein the length of the interior surface defining the passageway in the port engages the distal end of the sheath while the exterior surface is tapered and defines the annular channel.

10. The medical access device of claim 3, wherein the proximal portion is cylindrical.

11. The medical access device of claim 1, wherein the channel is sized to receive a full thickness of tissue, and has a width in a range of 1 mm to 7 mm, and a depth of 2 mm to 20 mm.

12. The medical access device of claim 1, wherein the channel has a depth to width ratio greater than about 1:1.

13. The medical access device of claim 1, wherein the port is permanently connected to the sheath.

14. The medical access device of claim 2, wherein the channel define opposing walls that are angled relative to a radial plane that is orthogonal to the longitudinal axis.

15. The medical access device of claim 1, wherein the channel has a depth greater than or equal to a width of the channel.

16. A medical system for accessing a bodily opening defined by tissue, the medical system comprising:
a medical access device having an elongated flexible sheath and a port connected to a distal end of the flexible sheath, the sheath defining a sheath lumen, the port having an interior surface defining a passageway and an exterior surface that is tapered towards the distal end, the passageway being in communication with the sheath lumen, the exterior surface defining an annular channel that opens radially, the port defining the tapered exterior surface and substantially filing the space between the interior surface of the port and the distal end of the flexible sheath;
the port defining a proximally facing pushing surface; and
a pusher defining a pusher lumen, the pusher and pusher lumen sized to receive the elongated flexible sheath within the pusher lumen and selectively abut the pushing surface, the medical system including a placement configuration where the pusher directly abuts the proximally facing pushing surface of the port.

17. The medical system of claim 16, wherein the passageway receives the distal end of the flexible sheath therein.

18. The medical system of claim 16, wherein the port projects radially from the flexible sheath to define the pushing surface.

19. The medical system of claim 16, wherein the pushing surface is formed on a proximal end surface of the port.

20. The medical system of claim 16, wherein the sheath lumen has a diameter in the range of 2 mm to about 20 mm.

21. The medical system of claim 16, wherein the port is a single piece separate from the sheath.

22. The medical access device of claim 16, wherein a largest outer diameter of the port is greater than an largest outer diameter of the sheath.

* * * * *